(12) United States Patent
Saunders et al.

(10) Patent No.: US 7,566,314 B2
(45) Date of Patent: *Jul. 28, 2009

(54) PORTABLE CERVICAL TRACTION DEVICE

(75) Inventors: H. Duane Saunders, Eden Prairie, MN (US); Mark R. Stultz, Minnetonka, MN (US)

(73) Assignee: The Saunders Group, Inc., Chaska, MN (US)

( * ) Notice: Subject to any disclaimer, the term of this patent is extended or adjusted under 35 U.S.C. 154(b) by 71 days.

This patent is subject to a terminal disclaimer.

(21) Appl. No.: 11/422,231

(22) Filed: Jun. 5, 2006

(65) Prior Publication Data

US 2006/0206046 A1 Sep. 14, 2006

Related U.S. Application Data

(63) Continuation of application No. 10/751,688, filed on Jan. 5, 2004, now Pat. No. 7,108,671, which is a continuation of application No. 10/320,589, filed on Dec. 16, 2002, now Pat. No. 6,899,690, which is a continuation of application No. 08/817,444, filed on Oct. 22, 1997, now Pat. No. 6,506,174, which is a continuation of application No. PCT/US95/14217, filed on Oct. 31, 1995, which is a continuation-in-part of application No. 08/334,189, filed on Nov. 3, 1994, now abandoned.

(51) Int. Cl.
*A61F 5/00* (2006.01)

(52) U.S. Cl. .......................................... 602/32; 128/870

(58) Field of Classification Search ................... 602/13, 602/18, 32–40; 128/845–846, 869–870

See application file for complete search history.

(56) References Cited

U.S. PATENT DOCUMENTS 1,205,649 A 11/1916 Miller (Continued)

FOREIGN PATENT DOCUMENTS

DE 2207647 8/1973

(Continued)

OTHER PUBLICATIONS

Product brochure, "Pronex™-A patient-controlled pneumatic device for the comfortable and secure management of cervical pain," Glacier Cross, Inc., 1 pg., undated.

(Continued)

*Primary Examiner*—Michael A. Brown
(74) *Attorney, Agent, or Firm*—Ropes & Gray LLP

(57) ABSTRACT

Low-cost, light weight portable cervical traction or spinal decompression devices for home use by a patient. A carriage is slidable along a portion of a support structure parallel to a longitudinal axis. The carriage includes a restraining mechanism adapted to releasably restrain a portion of a patient's body to the carriage. The pneumatic traction force generating apparatus is operatively coupled to move the carriage relative to the support structure when in a pressurized state. The pneumatic traction force generating apparatus is adapted to maintain a generally static traction force during a treatment period when in the pressurized state without additional pressurized air being supplied. A hand pump operated by the patient is fluidly connected to the pneumatic traction force generating apparatus to inject pressurized air. The hand pump is capable of injecting at least 138 kPa (20 psi) of pressure into the pneumatic traction force generating apparatus. A pressure relief mechanism operated by the patient is adapted to release pressure from the pneumatic traction force generating apparatus.

48 Claims, 10 Drawing Sheets

U.S. PATENT DOCUMENTS

| | | | |
|---|---|---|---|
| 1,242,688 A | 10/1917 | Hawley | |
| 1,803,556 A | 5/1931 | Nugent | |
| 2,273,088 A | 2/1942 | Byers | |
| 2,534,587 A | 12/1950 | Fisher et al. | |
| 2,554,337 A | 5/1951 | Lampert | |
| 2,689,127 A | 9/1954 | Silverton et al. | |
| 2,723,663 A | 11/1955 | Davis | |
| 2,733,712 A | 2/1956 | Wuesthoff | |
| 2,910,061 A | 10/1959 | Rabjohn | |
| 2,966,906 A | 1/1961 | Wiltrout | |
| 3,176,684 A | 4/1965 | Walsh | |
| 3,293,667 A | 12/1966 | Ohrberg | |
| 3,387,605 A | 6/1968 | Schmidt | |
| 3,413,971 A | 12/1968 | Evans | |
| 3,522,602 A | 8/1970 | Morton | |
| 3,548,817 A | 12/1970 | Mlttasch | |
| 3,554,189 A | 1/1971 | Hendrickson | |
| 3,561,434 A | 2/1971 | Kllbey | |
| 3,621,839 A | 11/1971 | Barthe | |
| 3,734,068 A | 5/1973 | Tucker et al. | |
| 3,734,088 A * | 5/1973 | Tucker et al. | 606/243 |
| 3,827,429 A | 8/1974 | Heikes | |
| 3,828,377 A | 8/1974 | Fary, Sr. | |
| 3,888,243 A | 6/1975 | Powlan | |
| 3,937,216 A * | 2/1976 | Brown | 602/32 |
| 4,024,860 A * | 5/1977 | Chelnokov et al. | 602/32 |
| 4,146,021 A | 3/1979 | Brosseau et al. | |
| 4,146,612 A | 3/1979 | Veber | |
| 4,166,459 A | 9/1979 | Nightingale | |
| 4,242,946 A | 1/1981 | Toliusis | |
| 4,320,749 A | 3/1982 | Highley | |
| 4,356,816 A | 11/1982 | Granberg | |
| 4,428,276 A | 1/1984 | Loveless | |
| 4,436,303 A | 3/1984 | McKillip et al. | |
| 4,466,427 A * | 8/1984 | Granberg | 606/243 |
| 4,579,109 A | 4/1986 | Lundblad | |
| 4,649,907 A | 3/1987 | Whitehead et al. | |
| 4,664,101 A | 5/1987 | Granberg | |
| 4,669,455 A | 6/1987 | Bellati | |
| 4,736,736 A | 4/1988 | Moers et al. | |
| 4,760,842 A | 8/1988 | Holmes | |
| RE32,791 E | 11/1988 | Saunders | |
| 4,805,603 A | 2/1989 | Cumberland | |
| 4,832,007 A | 5/1989 | Davis, Jr. et al. | |
| 4,866,796 A | 9/1989 | Robinson et al. | |
| 4,944,054 A | 7/1990 | Bossert | |
| 4,951,654 A | 8/1990 | Gambale et al. | |
| 4,981,034 A | 1/1991 | Haeg | |
| 4,981,148 A | 1/1991 | Fuller | |
| 4,991,572 A | 2/1991 | Chases | |
| 4,995,378 A * | 2/1991 | Dyer et al. | 606/241 |
| 5,052,378 A | 10/1991 | Chitwood | |
| 5,067,483 A | 11/1991 | Freed | |
| 5,092,322 A | 3/1992 | Gantz | |
| 5,169,160 A | 12/1992 | Gaskill et al. | |
| 5,181,904 A | 1/1993 | Cook et al. | |
| 5,306,231 A | 4/1994 | Cullum et al. | |
| 5,360,392 A | 11/1994 | McCoy | |
| 5,382,226 A | 1/1995 | Graham | |
| 5,441,479 A | 8/1995 | Chitwood | |
| 5,454,781 A | 10/1995 | Chitwood | |
| 5,474,086 A | 12/1995 | McCormick et al. | |
| 5,505,691 A | 4/1996 | Fenkell | |
| 5,569,175 A | 10/1996 | Chitwood | |
| 5,578,060 A | 11/1996 | Pohl et al. | |
| 5,662,597 A | 9/1997 | Chitwood | |
| 5,667,529 A | 9/1997 | Butner | |
| 5,709,649 A | 1/1998 | Chitwood | |
| 5,722,941 A | 3/1998 | Hart | |
| 5,916,188 A | 6/1999 | Ousdal | |
| 6,039,737 A | 3/2000 | Dyer | |
| 6,045,525 A | 4/2000 | Chitwood | |
| 6,059,548 A | 5/2000 | Campbell et al. | |
| 6,171,273 B1 | 1/2001 | Saunders | |
| 6,186,968 B1 | 2/2001 | Wu | |
| 6,447,468 B1 | 9/2002 | Hankins et al. | |
| 6,506,174 B1 * | 1/2003 | Saunders et al. | 602/33 |
| 6,899,690 B2 * | 5/2005 | Saunders et al. | 602/36 |
| 7,108,671 B2 * | 9/2006 | Saunders et al. | 602/32 |
| 2004/0171974 A1 | 9/2004 | Emsky | |

FOREIGN PATENT DOCUMENTS

| | | |
|---|---|---|
| DE | 2622255 | 11/1977 |
| FR | 997691 | 1/1952 |
| GB | 716904 | 10/1954 |

OTHER PUBLICATIONS

Product brochure, "Pneu-trac™, Air Pressure the Patient Controls," Zinco Industries, Inc., 1 pg., undated.

"Spinal Traction," Evaluation, Treatment and Prevention of Musculoskeletal Disorders, Chapter 10, pp. 275-302, undated.

Decision of the United States Court of Appeals for the Federal Circuit, 2006-1576, *The Saunders Group, Inc.* v. *Comfortrac, Inc.*, and Care Rehab and Orthopaedic Products Inc., Decided: Jun. 27, 2007 (16 pages).

\* cited by examiner

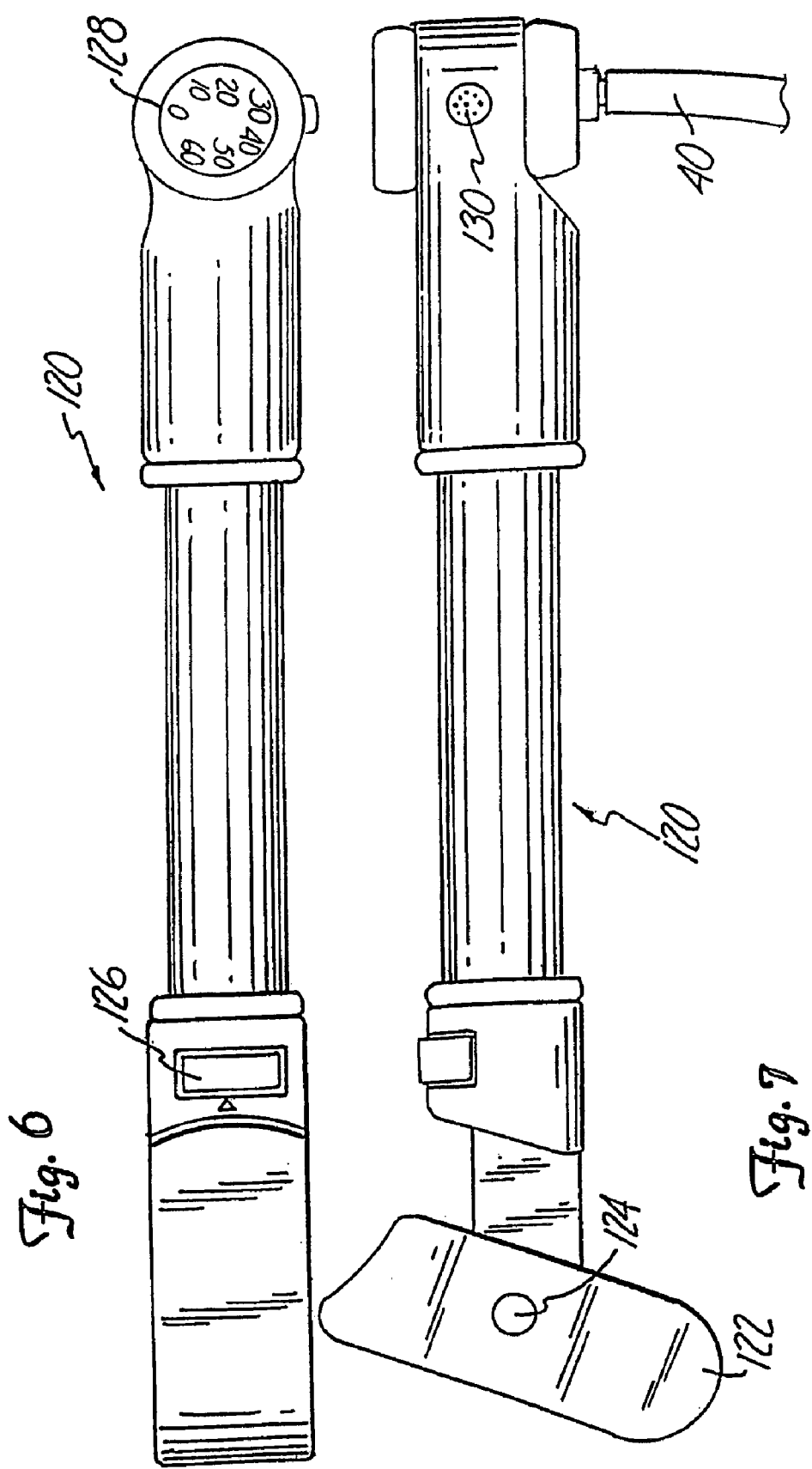

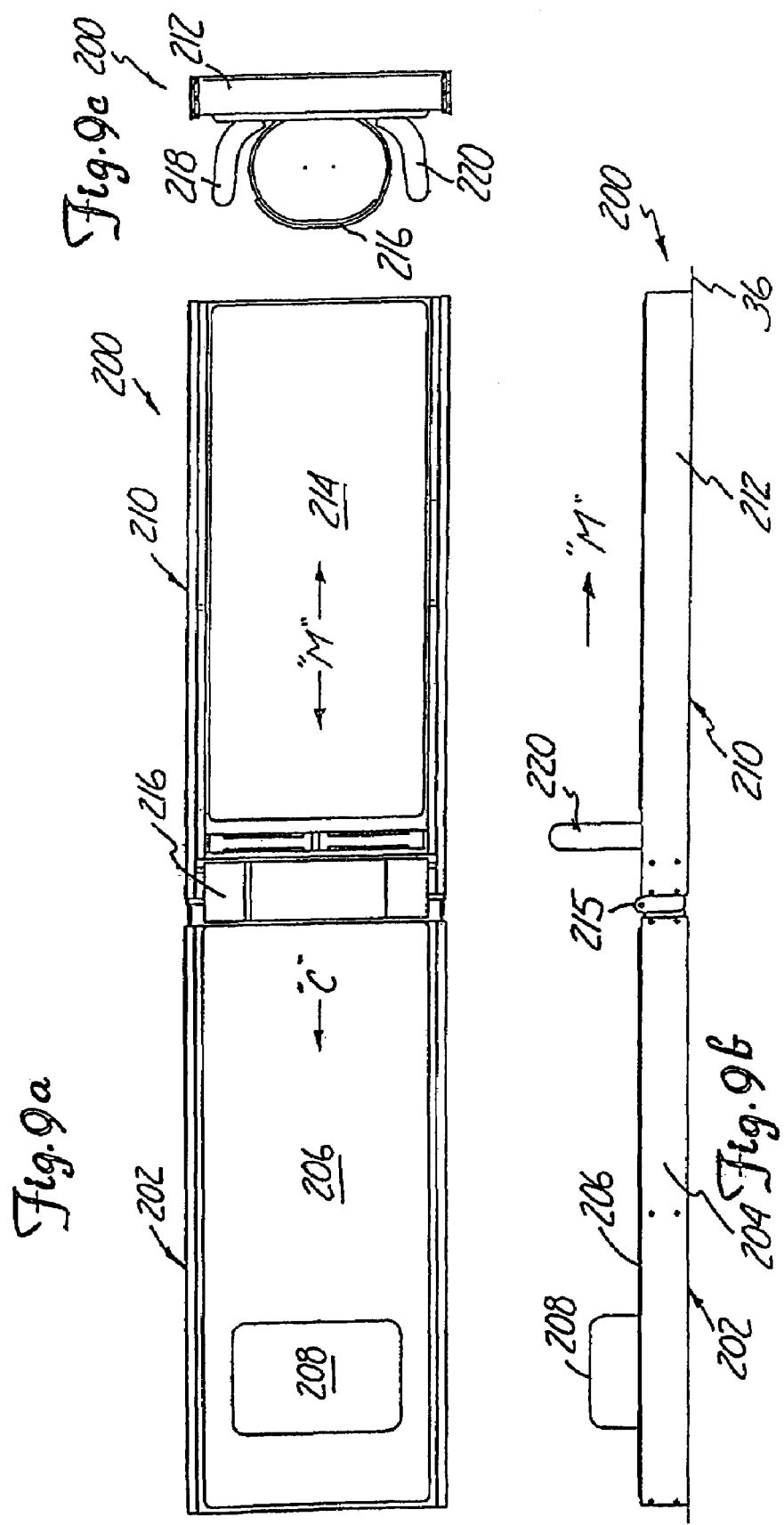

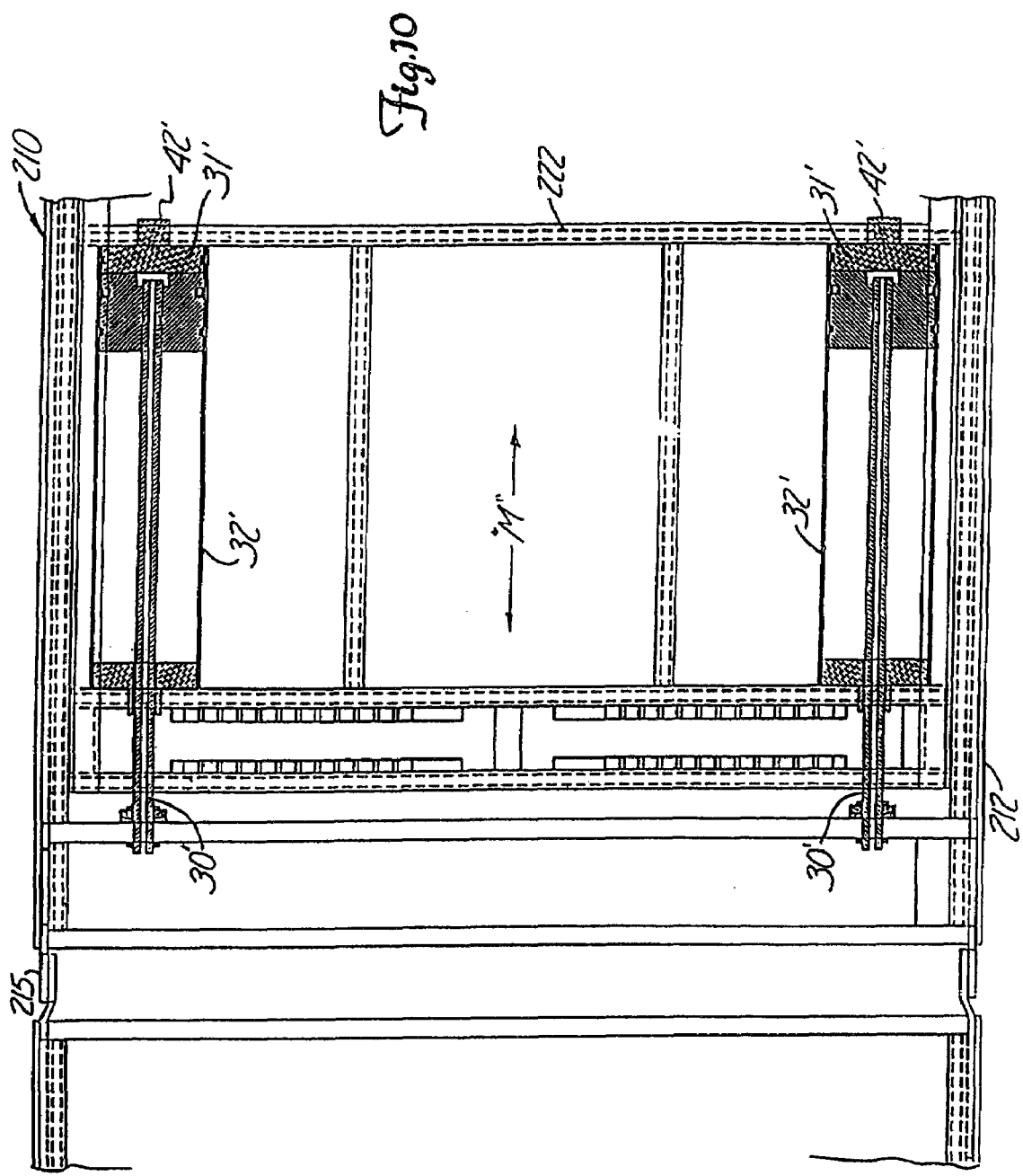

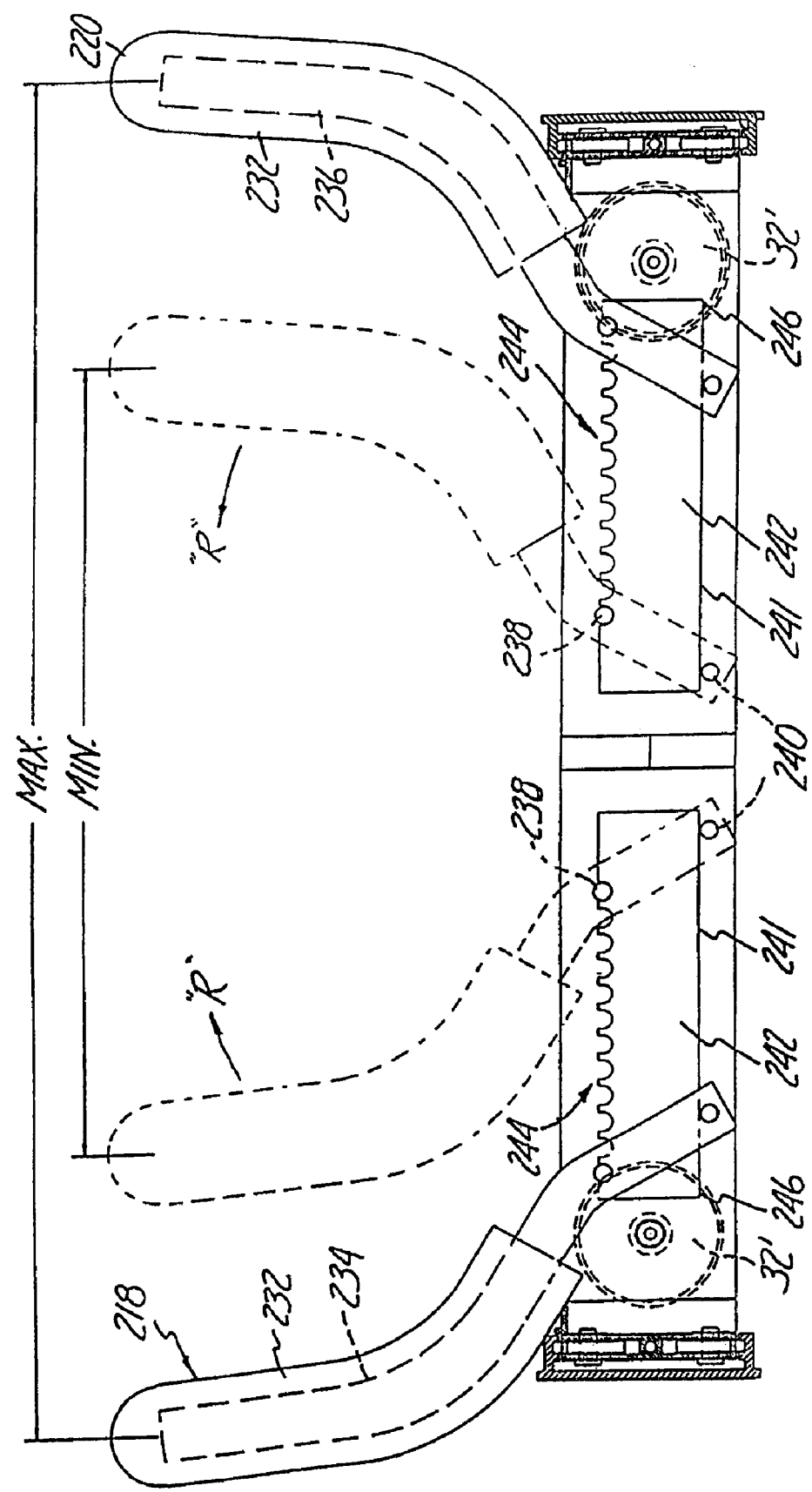

PORTABLE CERVICAL TRACTION DEVICE

RELATED APPLICATIONS

The present application is a continuation of U.S. patent application Ser. No. 10/751,688 filed Jan. 5, 2004 (allowed); which is a continuation of U.S. patent application Ser. No. 10/320,589 filed Dec. 16, 2002 (U.S. Pat. No. 6,899,690), which is a continuation of U.S. patent application Ser. No. 08/817,444 (U.S. Pat. No. 6,506,174), which is a continuation of PCT/US95/14217 filed Oct. 31, 1995, which claims priority to and is a continuation-in-part of U.S. patent application Ser. No. 08/334,189 filed Nov. 3, 1994 (abandoned), all of which are hereby incorporated by reference.

FIELD OF THE INVENTION

The present invention is directed to a portable traction device powered by a pneumatic traction force generating apparatus.

BACKGROUND OF THE INVENTION

Traction, also referred to as spinal decompression, is widely used to relieve pressure on inflamed or enlarged nerves. While traction is applicable to any part of the body, cervical and lumbar or spinal traction are the most common. When correctly performed, spinal traction can cause distraction or separation of the vertebral bodies, a combination of distraction and gliding of the facet joints, tensing of the ligamentous structures of the spinal segment, widening of the intervertebral foramen, straightening of spinal curvature and stretching of the spinal musculature. Depending on the injury being treated, the traction component of physical therapy may require multiple sessions per week for a prolonged period of time.

Cervical traction requires a traction force up to approximately 222 N (50 lbs.). Lumbar traction typically requires force equal to half of the patient's bodyweight, or about 333-667 N (75-150 lbs.). The equipment necessary for performing traction, however, has typically been expensive and thus only available to a patient in a therapist's office.

Attempts to create a sufficiently low cost portable traction device for home use have thus far produced unsatisfactory results. A number of portable traction devices utilize pneumatic or hydraulic cylinders to create the traction force. Hydraulic cylinders have the disadvantage of the weight of the hydraulic fluid. Pneumatic cylinders with low pressure inputs typically can not maintain an adequate traction force for a sufficient period of time to be effective in a traction device. In an attempt to overcome this deficiency, some of these devices utilize an automatic pumping device triggered by a pressure sensing device to supply additional compressed air so that a constant level of traction force is maintained. These pump and sensor configurations add cost, weight and complexity to the traction device.

The air input pumps used on some traction devices also exhibit a number of shortcomings. For example, bulb-type air pumps produce relatively small input pressures. A small female patient can generate only about 483 kPa (7 psi) of pressure using a bulb-type pump. Consequently, small input pressure devices require large diameter cylinders to generate the necessary output traction forces. Larger diameter cylinders, when used with low pressure input devices, are more prone to leak, thereby further complicating the problem of maintaining a constant traction force for a prolonged period of time.

Therefore, what is needed is a low cost, light weight portable traction device utilizing a pneumatic traction force generating apparatus that can maintain a traction force of an adequate magnitude for a prolonged period of time.

BRIEF SUMMARY OF THE INVENTION

The present invention is directed to portable cervical traction or spinal decompression devices powered by a pneumatic traction force generating apparatus. The present invention is also directed to pneumatic traction force generating apparatuses suitable for use in traction or spinal decompression devices.

One embodiment of the claimed invention is directed to a low-cost, light weight portable cervical traction device for home use by a patient. A carriage is slidable along a portion of a support structure parallel to a longitudinal axis. The carriage includes a restraining mechanism adapted to releasably restrain a portion of a patient's body to the carriage. The pneumatic traction force generating apparatus includes at least one pneumatic chamber and at least one air inlet. The pneumatic traction force generating apparatus is operatively coupled to move the carriage relative to the support structure when the at least one pneumatic chamber is in a pressurized state. The pneumatic traction force generating apparatus is adapted to maintain a generally static traction force during a treatment period when in the pressurized state without additional pressurized air being supplied. A hand pump operated by the patient is fluidly connected to the pneumatic traction force generating apparatus to inject pressurized air into the at least one pneumatic chamber. The hand pump is preferably capable of injecting at least 138 kPa (20 psi) of pressure into the pneumatic chamber. A pressure relief mechanism operated by the patient is adapted to release pressure from the pneumatic traction force generating apparatus.

The carriage preferably includes a head support pad adapted to receive the patient's head. The restraining mechanism is preferably a pair of opposing neck supports contoured and arranged to engage the occipital area of the patient's head when the head is on the head support pad. The lateral separation between the opposing neck support is preferably adjustable.

The pneumatic traction force generating apparatus is preferably capable of maintaining a generally static traction force of greater than 111 N (25 pounds) for a period in excess of 10 minutes without additional pressurized air being injected into the at least one pneumatic chamber. In another embodiment, the pneumatic traction force generating apparatus is capable of maintaining a generally static traction force of greater than 200 N (45 pounds) for a period in excess of 20 minutes without additional pressurized air being injected into the at least one pneumatic chamber. In one embodiment, the treatment period is at least 10 minutes.

The present traction device optionally includes a gauge indicating traction force and/or at least one pressure regulator adapted to prevent the pressure in the pneumatic traction force generating apparatus from exceeding a predetermined value. A pressure relief mechanism operated by the patient is preferably incorporated in the user operated hand pump.

The pneumatic traction force generating apparatus can optionally include at least one pneumatic cylinder. In one embodiment, the at least one pneumatic cylinder optionally includes at least one pressure activated seal in the pneumatic cylinder extending circumferentially around a piston. In this embodiment, the pressure activated seal is movable between a relaxed position and an extended position so the pressure activated seal engages an internal surface on the pneumatic cylinder when the pneumatic cylinder is in the pressurized state.

In another embodiment of the claimed invention, the pneumatic traction force generating apparatus includes at least one pneumatic cylinder operatively coupled to move the carriage along the track relative to the support structure when in a pressurized state. The at least one pneumatic cylinder maintains a generally static traction force during a treatment period when in the pressurized state without additional pressurized air being supplied.

In another embodiment of the claimed invention, the pneumatic traction force generating apparatus includes at least one pneumatic cylinder having a first end and a moveable piston at a second end. One of the pneumatic cylinder or the piston is operatively coupled to a support structure and the other is operatively coupled to the carriage. The pneumatic traction force generating apparatus is adapted to move the carriage along the track relative to the support structure when in a pressurized state and to maintain a generally static traction force during a treatment period when in the pressurized state without additional pressurized air being supplied.

In another embodiment of the claimed invention, the pneumatic traction force generating apparatus includes at least one air inlet. The pneumatic traction force generating apparatus is operatively coupled to move the carriage relative to the support structure when in a pressurized state. The pneumatic traction force generating apparatus is adapted to maintain a generally static traction force during a treatment period when in the pressurized state without additional pressurized air being supplied.

BRIEF DESCRIPTION OF THE SEVERAL VIEWS OF THE DRAWING

FIG. 6 is a top view of an exemplary air pump;
FIG. 7 is a side view of the exemplary air pump of FIG. 6;
FIGS. 9a-9c illustrate a top, front and end view of an alternate portable lumbar traction device;
FIG. 10 illustrates a pneumatic cylinder configuration for use with a portable, lumbar traction device;
and
FIG. 11 illustrates a hip gripping device for a portable, lumbar traction device.

DETAILED DESCRIPTION OF THE PREFERRED EMBODIMENT

Figure 1:
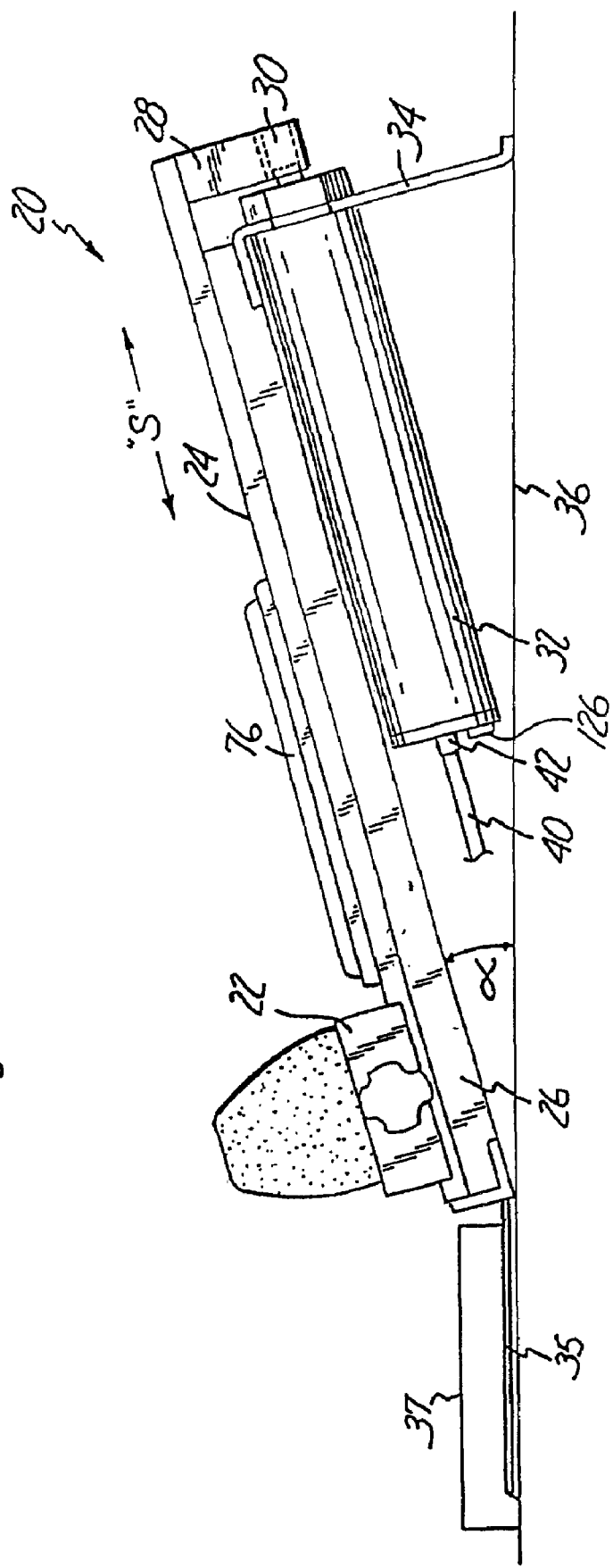
FIG. 1 is a side view of a portable traction device.
Figure 2:
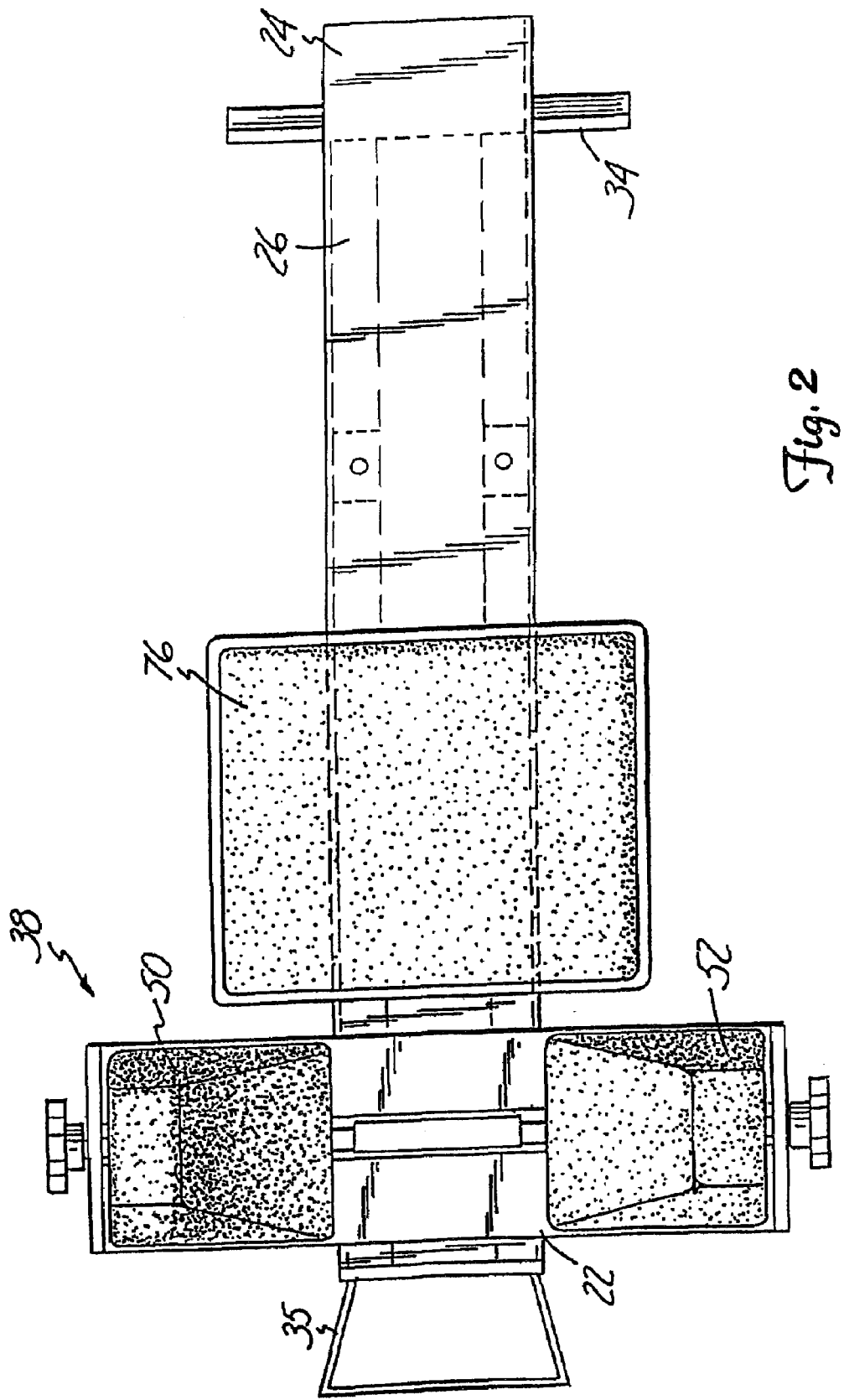
FIG. 2 is a top view of the portable traction device of FIG. 1.
Figure 3:
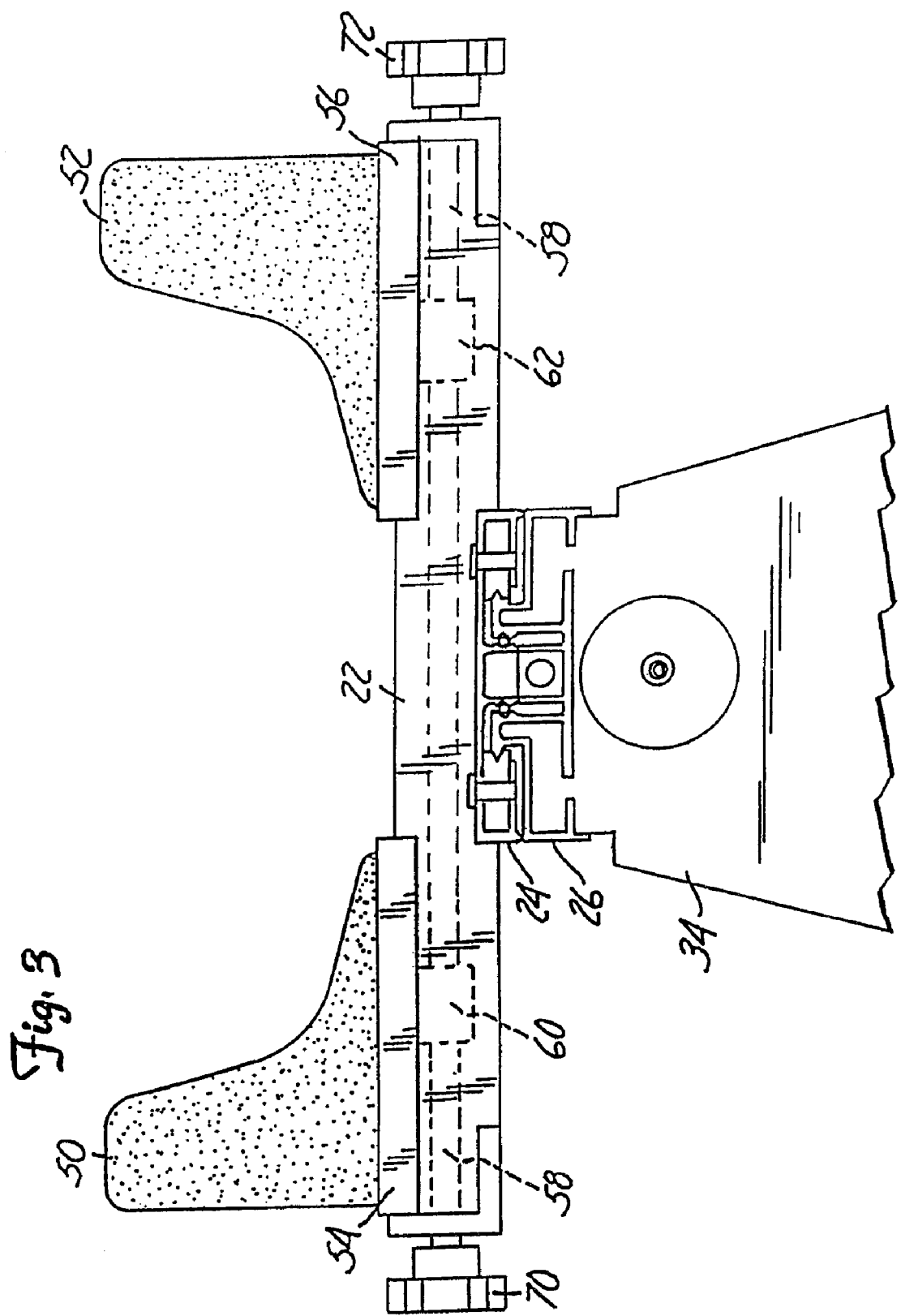
FIG. 3 is an end view of the portable traction device of FIG. 1 illustrating a laterally adjustable neck support.

FIGS. 1 and 2 illustrate an exemplary portable, cervical traction device 20 in which a carriage 22 and slide portion 24 are allowed to move freely on a track 26 along a direction "S" (see also FIG. 3). The slide portion 24 includes a slide bracket 28 which engages with a piston rod 30 on a pneumatic cylinder 32 mounted underneath the track 26. A lateral adjustment mechanism 38, a head support pad 76, and a pair of V-shaped neck supports 50, 52 (see FIG. 3), are mounted to the carriage 22, which will be discussed in detail below. The pneumatic cylinder 32 is attached to the track 26 by an angle bracket 34. An air line 40 is attached to an air inlet 42 at one end of cylinder 32 for providing pressurized air to the cylinder 32. An alternate V-shaped neck support structure suitable for use in the present invention is disclosed in U.S. Pat. No. Re. 32,791 issued to Saunders on Nov. 29, 1988, which is hereby incorporated by reference.

The angle bracket 34 also serves the purpose of retaining the track 26 at an angle α relative to a support surface 36. A removable stabilizer bracket 35 may optionally be added to prevent the support bracket 36 from lifting off of the support surface 36 during use. A pad 37 preferably is placed over the support bracket 36 for the comfort of the user. It will be understood that the length of the angle bracket 34 may be adjustable depending on the application of the portable traction device 20. For example, the angle bracket 34 may be of a telescoping constructions. It will also be understood that the slide portion 24 may engage with the track 26 in a variety of configurations, and that the present invention is not limited to the specific embodiment disclosed herein. The track 26, carriage 22, and slide portions 24 are preferably constructed of a lightweight, low cost material, such as, for example, aluminum, steel, high density plastic, or a variety of composite materials.

FIG. 3 is an end view of the lateral adjustment mechanism 38 on the carriage 22. Left and right neck supports 50, 52 form a V-shaped neck support structure that generally follows the contour of the base of the user's skull. The neck supports 50, 52 are attached to a pair of corresponding lateral slides 54, 56 on the carriage 22. The lateral slides 54, 56 are engaged with the threaded shaft 58 by a pair of coupler nuts 60, 62. The portion of the shaft 58 proximate coupler nut 60 has left-hand threads and the portion proximate coupler nut 62 has right-hand threads. The lateral position of the V-shaped neck supports 50, 52 is adjusted by turning the left and right knobs 70, 72. The neck supports 50, 52 are ideally positioned around the patient's head so that they contact and follow the contour of the occipital bone at the base of the patient's skull, while the back of the patient's skull rests on the head support pad.

Figure 4:
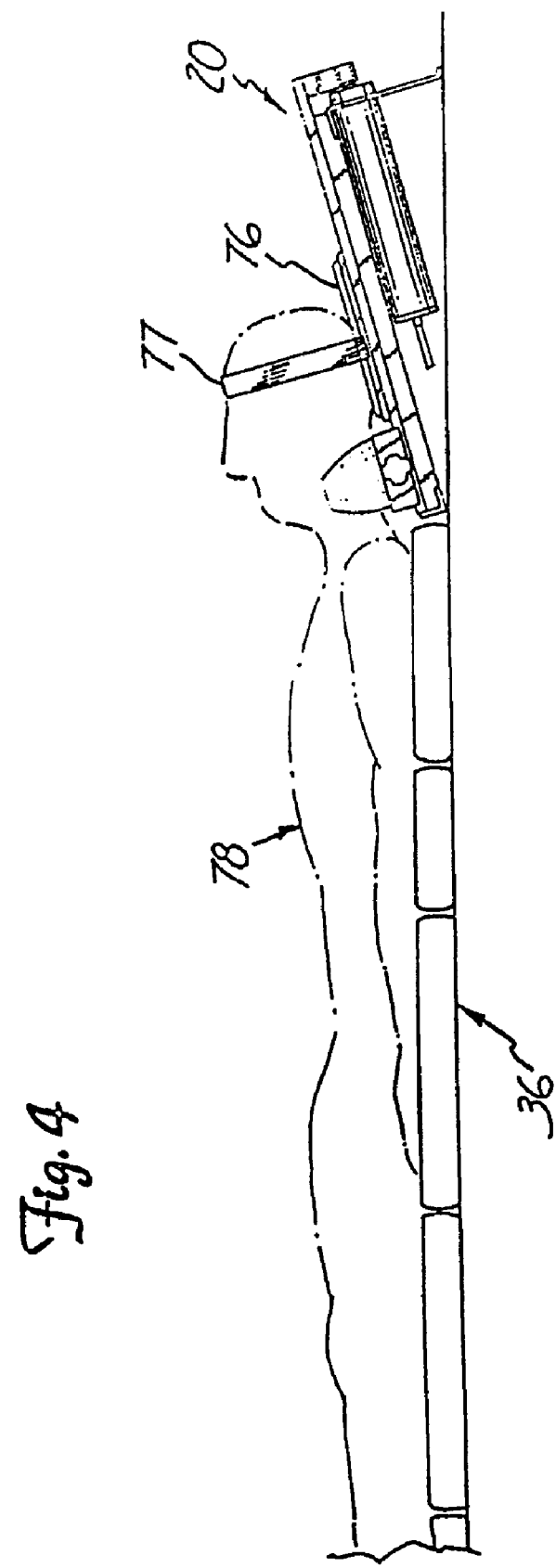
FIG. 4 is a side view of a patient utilizing the traction device of FIG. 1.

FIG. 4 illustrates a patient 78 utilizing the portable traction device 20 on a support surface 36. It will be understood that the present portable traction device 20 may be used on a variety of support surfaces, such as for example, a floor, a table, or any other suitable surface. It will also be understood that the support surface 36 does not necessarily have to be horizontal and that it may be desirable to have an angled support surface for some types of traction. A support strap 77 may optionally be used to restrain the patient's head to the head support pad 76 during traction.

Figure 5:
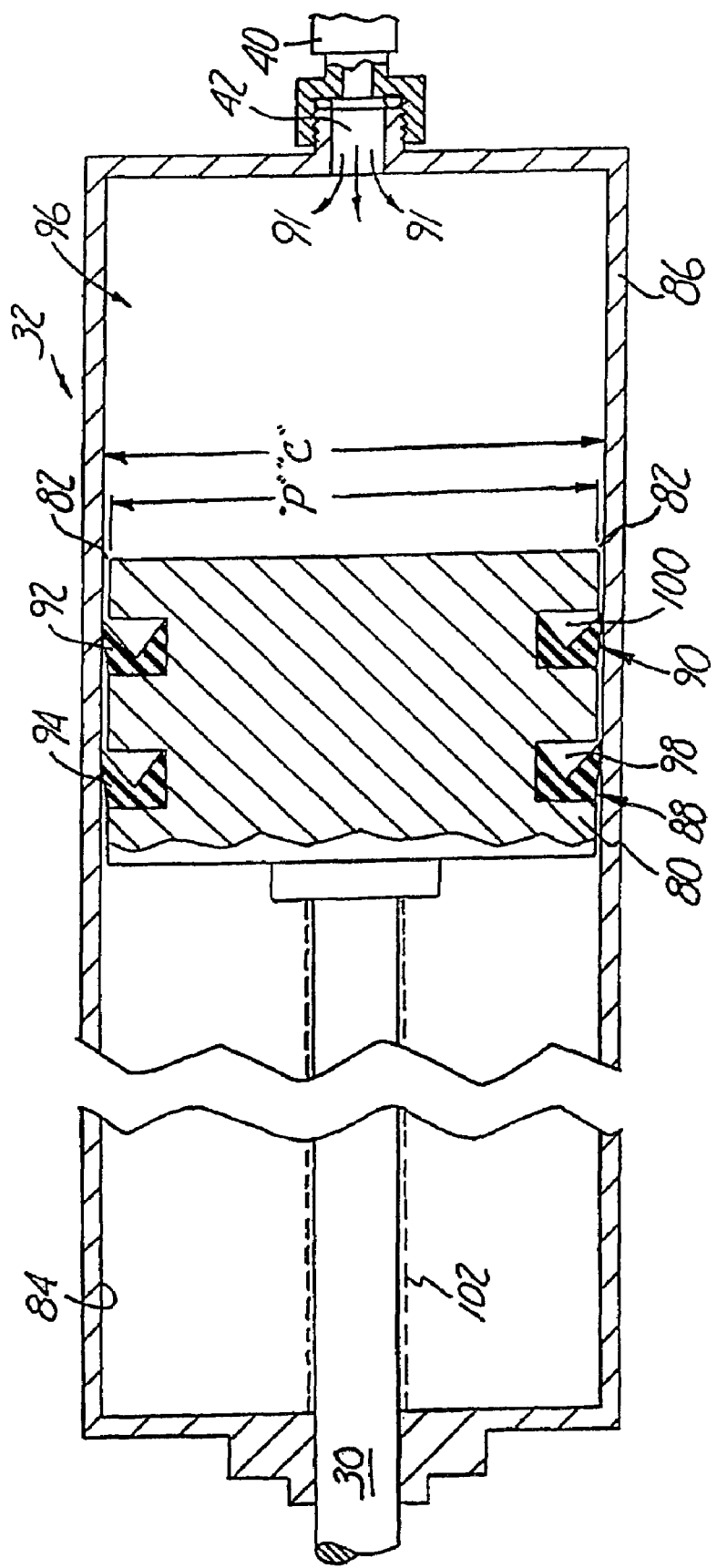
FIG. 5 is a schematic illustration of an exemplary pneumatic cylinder for use with a portable traction device.

The exemplary embodiment of FIG. 5 is a schematic illustration of a single-acting pneumatic cylinder 32 for use with a present portable traction device. In the exemplary embodiment of FIG. 5, piston 80 has a diameter "P" which is slightly smaller than the inside diameter "C" of the cylinder 32 so that a small gap 82 is formed between the piston 80 and inner surface 84 of cylinder wall 86. A pair of slots 88, 90 extending around the outside perimeter of the piston 80 contain a pair of pressure activated seals 92, 94. The seals 92, 94 are pre-shaped to form seal cavities 98, 100 facing upstream of the piston rod 30. It will be understood that the seals 92, 94 and seal cavities 98, 100 in the exemplary embodiment of FIG. 5 may be a variety of shapes.

In the exemplary embodiment of FIG. 5, the seals 92, 94 are arranged so that as pressurized air 91 enters the air inlet 42, and input chamber 97 is pressurized, a seal cavities 98, 100 are pressurized and the pressure activated seals 92, 94 are forced into engagement with the inside surface 84 of the cylinder wall 86. In the exemplary embodiment disclosed herein, approximately 13.8 kPa (2 psi) is required to engage the seals 92, 94 with the inside surface 84. Seal 94 is intended to capture blow-by air that passes the first seal 92. The small gap 82 between the cylinder wall 86 and the piston 80 permits generally uniform circumferential pressurization of the seals 92, 94 against the inside surface 84 around the entire circumference, thereby enhancing sealing capabilities. The pressure activated seal of the present pneumatic cylinder 32 in the exemplary embodiment of FIG. 5 is capable of maintaining a static traction force of greater than 111 N (25 lbs.) for a period in excess of 10 minutes, and preferably, a static traction force of greater than 200 N (45 lbs.) for a period in excess of 20 minutes, without the need to supply additional pressurized air.

When the pressure in input chamber 97 is released, the seals 92, 94 in the exemplary embodiment of FIG. 5 disengage from the inside surface 84 and the piston 80 is allowed to move freely within the cylinder 32. The pneumatic cylinder 32 may include spring or other resilient compression member 102 around the piston rod 30 to urge the piston 80 back toward the air inlet 42 when the compressed air 91 is released. Alternatively, a spring (not shown) may be positioned between the slide portion 24 and the track 26. The compression member 102 preferably has a low spring forces so as to minimize the amount of force needed for the patient to activate the cylinder.

FIGS. 6 and 7 illustrate an exemplary air pump 120 for use with the present portable traction device 20. The air pump 120 has a T-handle 122 attached at one end by a pivot point 124. The T-handle 122 configuration offers ergonomic advantages over a standard straight pump handle. Alternatively, a straight handle may be substituted for the T-handle. An adjustable pressure regulator 126 may optionally be included in the pump 120 or cylinder 32 (see FIG. 1) so that over-pressure situations can be prevented. The other end of the air pump 120 includes a gauge 128, which preferably is calibrated to read the actual amount of traction force being provided to the patient, rather than pounds per square inch. The pump, handle and gauge may be formed as a singled piece by an injection molding process.

A manual pressure relief mechanism 130 is also located proximate the gauge 128 for relieving the pressure in the pneumatic cylinder 32 when the treatment period is completed. Alternatively, the pressure relief mechanism (not shown) may be operated by rotating the gauge 128. Air tube 40 is connected to the air pump 120 opposite the gauge 128. A variety of pressure regulator configurations may be used in the present invention. For example, the pressure gauge 128 may include an internal pressure regulator.

To use the portable, cervical traction device 20, it is placed on a suitable support surface 36. The left and right knobs 70, 72 are rotated to allow the neck of the user to fit easily between the left and right neck supports 50, 52. The slide portion 24 is moved down on the track 26 as far as possible by depressing pressure relief mechanism 130 (see FIG. 7) until cylinder 32 is at atmospheric pressure.

The back of the user is placed on the support surface 36 so that the neck is cradled by the neck supports 50, 52. The neck supports 50, 52 should initially contact the user in the mid cervical region, midway between the tip of the earlobe and the top of the shoulder. The knobs 70, 72 are turned until the neck supports 50, 52 are moved firmly against both sides of the neck. The user's head is secured to the head support pad 76 by the support strap 77. With the head support pad 76 under the shoulders, the user's head should be nearly aligned with the spine.

The user then slowly pumps air into the cylinder 32 using the air pump 120. The configuration of the pump 120 permits a patient to simultaneously view the gauge 128 and operate the pump, while inclined in the portable traction device 20. The gauge 128 allows the user to stay within the pressure/traction force guidelines provided by the health care provider. The patient increases the traction force by manually operating the pump 120 or decreases the traction force by manually pressing the pressure relief mechanism 130. The neck supports 50, 52 are properly positioned when there is solid contact at the base of the head and the supports 50, 52 are positioned near the tip of the ear lobes. When the treatment is complete, the traction force is released by pressing and holding the pressure relief mechanism 130 on the air pump 120.

Figure 8:
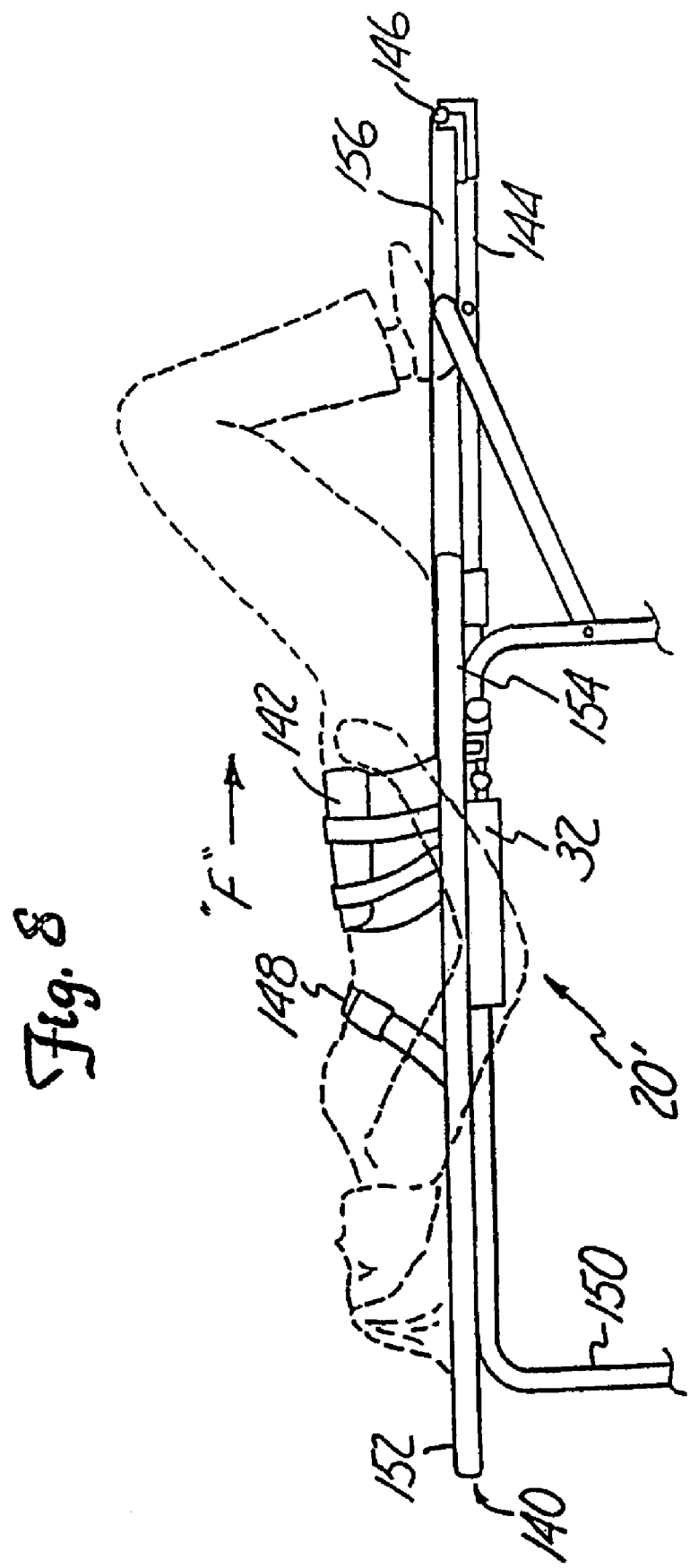
FIG. 8 illustrates an exemplary portable, lumbar traction device.

FIG. 8 illustrates a portable, lumbar traction device 140 in which the pneumatic cylinder 32 is attached to a portable traction device 140. The portable, lumbar traction device 140 includes a frame 150 retaining a support surface 152. In a first embodiment, a pelvic belt 142 retains the patient's pelvis to a sliding portion 154, which slides along track 156. The pneumatic cylinder 32 mounted to the frame 150 is coupled to the sliding portion 154 so that the sliding portion 154 moves along the track 156, creating a traction force "F" when the cylinder 32 is pressurized. A counter traction belt 148 provides a passive counter traction force on the patient's lower rib cage. The pneumatic cylinder 32 preferably maintains a static traction force of greater than 445 N (100 lbs.) for a period in excess of 10 minutes, and preferably, a static traction force of greater than 890 N (200 lbs.) for a period in excess of 20 minutes, without the need to supply additional pressurized air. It will be understood that two cylinders may be necessary to achieve a static traction force in excess of 445 N.

In a second embodiment, pelvic belt 142 is engaged with the pneumatic cylinder 32 by a cable 144 and pulley 146 configuration mounted at the foot of the portable traction device 140. Counter-traction belt 148 provides a passive counter traction force on the patient's lower rib cage to restrain the patient in a fixed position relative to the portable traction device 140. When the patient activates the pneumatic cylinder 32 as discussed above, the cable 144 is retracted, creating a traction force "F" on the waist belt 142 and the patient's pelvic region. In either of the above embodiments, the counter traction belt 148 may also be coupled to the pneumatic cylinder 32 to provide an active counter traction force in a direction opposite to "F" on the patient.

FIGS. 9a-9c illustrate an alternate embodiment of a portable, lumbar traction device 200 positioned directly on the support surface 36. Upper body support platform 202 includes a frame 204 supporting a support surface 206. A moveable head rest 208 is positioned on the surface 206. Lower body support platform 210 has a support surface 214 slidably engaged with frame 212. The surface 214 on the lower body support platform 210 slides in a direction "M" preferably about 0.15 meters under the force of a pair of pneumatic cylinders 32' (see FIG. 10). The upper and lower body support platforms 202, 210 are connected by a hinge 215 to facilitate shipping and storage of the lumbar traction device 200.

An adjustable rib gripping belt 216 is attached to the upper body support platform 202 to provide a passive counter traction force in a direction "C". A pair of laterally adjustable hip gripping supports 218, 220 are connected to the surface 214 so that they move in the direction "M" with the surface 214. The hip gripping supports 218, 220 are independently adjustable and curved to generally correspond to the shape of the user's waist, as will be discussed in connection with FIG. 11.

FIG. 10 illustrates a segment of the frame 212 of the lower body support platform 210. The piston rods 30' of the pneumatic cylinders 32' are engaged with the frame 210. Cylinder heads 31' are attached to sliding support structure 222 that supports surface 214. Introduction of pressurized air through the air inlet 42' moves the sliding support structure 222 and support surface 214 in the direction "M". The operation of the cylinders 32' is substantially as discussed above in connection with FIGS. 5-7. The pair of cylinders 32' maintain a static traction force of at least 890 N (200 lbs.) for a period in excess of 20 minutes, without the need to supply additional pressurized air.

FIG. 11 illustrates a hip gripping device 230 for use with the portable, lumbar traction devices 20' and 200 of the present invention. The hip gripping supports 218, 220 are shown in both the maximum and minimum lateral positions. In the exemplary embodiment illustrated in FIG. 11, the maximum and minimum lateral positions correspond to a distance of 0.50 m and 0.29 m, respectively. However, it will be understood that the hip gripping device may be modified to accommodate larger and smaller users.

The hip gripping supports 218, 220 include rigid curved members 234, 236 covered with padding material 232 for the comfort of the user. The curves generally follow the contour of the waist of the human body. Suitable padding material include high density foam, rubber or a variety of elastomeric materials. The rigid curved members 234, 236 include a pin 238 positioned to engage with receiving slots 244 on the top of the track 242 and a pin 240 positioned to engage with the bottom surface 241 of the track 242. To adjust the hip gripping device 230, the user rotates one or both of the hip gripping supports 218, 220 in the direction "R" so that the pin 238 disengages from the slots 244. While in the rotated position, the hip gripping supports 218, 220 may be moved laterally along the track 242 to the desired location. Rotating the hip gripping supports 218, 200 in the direction opposite to "R" will engage the pin 230 with one of the slots 244. The hip gripping supports 218, 220 may be completely disengaged from the track 242 by moving the pin 240 past the ends 246 of the track 242 near the cylinders 32' and lifting the supports 218, 220 upward. It will be understood that the waist belt 142 of FIG. 8 may be substituted for the hip gripping device 230.

To use the portable, lumbar traction device 200, it is placed on a suitable support surface 36. The hip gripping supports 218, 220 are positioned to firmly, but comfortably, engage the waist of the user. The support surface 214 of the lower body support platform 210 is moved upward toward the upper body support platform 202 as far as possible by depressing the pressure relief mechanism 130 (see FIG. 7) until cylinders 32' are at atmospheric pressure.

The back of the user is placed on the support surface 206 so that the waist is cradled by the hip gripping supports 218, 220. The hip gripping supports should initially contact the user midway between the bottom of the rib cage and the top of the pelvis. The user's chest is secured to the support surface 206 of the upper body support platform 202 by the rib gripping belt 216. The head rest 208 should be placed under the user's head. The user then slowly pumps air into the cylinders 32' using the air pump 120, as discussed in connection with the portable, cervical traction device 20. The hip gripping supports 218, 220 are properly positioned when there is solid contact with the top of the pelvis.

The present invention has now been described with reference to the several embodiments thereof. It will be apparent to those skilled in the art that many changes can be made in the embodiments described without departing from the scope of the invention. Thus, the scope of the present invention should not be limited to the structures described herein, but only by structures described by the language of the claims and the equivalents of those structures. For example, the present portable traction device may be arranged in a variety of configurations to facilitate traction to any part of the body.

What is claimed is:

1. A low-cost, light weight portable cervical traction device for home use by a patient comprising:
 a support structure having a longitudinal axis;
 a carriage slidable along a portion of the support structure parallel to the longitudinal axis, the carriage comprising a head support pad adapted to receive a patient's head and the restraining mechanism comprises a pair of opposing neck supports contoured and arranged to engage the occipital area of the patient's head when the head is on the head support pad, the restraining mechanism adapted to releasably restrain a portion of a patient's body to the carriage;
 a pneumatic traction force generating apparatus comprising at least one pneumatic chamber and at least one air inlet, the pneumatic traction force generating apparatus operatively coupled to move the carriage relative to the support structure when the at least one pneumatic chamber is in a pressurized state, the pneumatic traction force generating apparatus adapted to maintain a generally static traction force during a treatment period when in the pressurized state without additional pressurized air being supplied;
 a hand pump operated by the patient fluidly connected to the pneumatic traction force generating apparatus to inject pressurized air into the at least one pneumatic chamber, the hand pump is capable of injecting at least 138 kPa (20 psi) of pressure into the pneumatic chamber; and
 a pressure relief mechanism operated by the patient adapted to release pressure from the pneumatic traction force generating apparatus.

2. The apparatus of claim 1 wherein the restraining mechanism comprises a pair of opposing neck supports adjustably attached to the carriage to permit adjustment of the lateral separation there between.

3. The apparatus of claim 1 wherein the pneumatic traction force generating apparatus is capable of maintaining a generally static traction force of greater than 111 N (25 pounds) for a period in excess of 10 minutes without additional pressurized air being injected into the at least one pneumatic chamber.

4. The apparatus of claim 1 wherein the pneumatic traction force generating apparatus is capable of maintaining a generally static traction force of greater than 200 N (45 pounds) for a period in excess of 20 minutes without additional pressurized air being injected into the at least one pneumatic chamber.

5. The apparatus of claim 1 comprising a gauge indicating traction force.

6. The apparatus of claim 1 comprising at least one pressure regulator adapted to prevent the pressure in the at least one pneumatic chamber from exceeding a predetermined value.

7. The apparatus of claim 1 wherein the pressure relief mechanism is incorporated in the hand pump.

8. The apparatus of claim 1 wherein the pneumatic traction force generating apparatus comprises at least one pneumatic cylinder.

9. The apparatus of claim 1 wherein the pneumatic traction force generating apparatus comprises at least one pneumatic cylinder including at least one pressure activated seal.

10. The apparatus of claim 1 wherein the pneumatic traction force generating apparatus comprises at least one pneumatic cylinder and at least one pressure activated seal in the pneumatic cylinder extending circumferentially around a piston, the pressure activated seal movable between a relaxed position and an extended position so the pressure activated seal engages an internal surface on the pneumatic cylinder when the pneumatic cylinder is in the pressurized state.

11. The apparatus of claim 1 wherein the treatment period comprises at least 10 minutes.

12. A low-cost, light weight portable cervical traction device for home use by a patient comprising:
- a support structure having a longitudinal axis;
- a carriage slidable along a portion of the support structure parallel to the longitudinal axis, the carriage comprising a head support pad adapted to receive a patient's head and the restraining mechanism comprises a pair of opposing neck supports contoured and arranged to engage the occipital area of the patient's head when the head is on the head support pad, the restraining mechanism adapted to releasably restrain a portion of a patient's body to the carriage;
- a pneumatic traction force generating means for moving the carriage relative to the support structure when the pneumatic traction force generating means is in a pressurized state and for maintaining a generally static traction force during a treatment period when in the pressurized state without additional pressurized air being supplied;
- a hand pump operated by the patient fluidly connected to the pneumatic traction force generating means for injecting pressurized air, the hand pump is capable of injecting at least 138 kPa (20 psi) of pressure into the pneumatic traction force generating means; and
- a pressure relief mechanism operated by the patient adapted to release pressure from the pneumatic traction force generating means.

13. A low-cost, light weight portable cervical traction device for home use by a patient comprising:
- a support structure having a track;
- a carriage slidable along a portion of the track, the carriage comprising a head support pad adapted to receive a patient's head and the restraining mechanism comprises a pair of opposing neck supports contoured and arranged to engage the occipital area of the patient's head when the head is on the head support pad, the restraining mechanism adapted to releasably restrain a portion of a patient's body to the carriage;
- a pneumatic traction force generating apparatus comprising at least one pneumatic cylinder operatively coupled to move the carriage along the track relative to the support structure when in a pressurized state, the at least one pneumatic cylinder maintains a generally static traction force during a treatment period when in the pressurized state without additional pressurized air being supplied;
- a hand pump operated by the patient fluidly connected to the at least one pneumatic cylinder and adapted to inject pressurized air into the at least one pneumatic cylinder; and
- a pressure relief mechanism operated by the patient adapted to release pressure from the at least one pneumatic cylinder.

14. The apparatus of claim 13 wherein the restraining mechanism comprises a pair of opposing neck supports adjustably attached to the carriage to permit adjustment of the lateral separation there between.

15. The apparatus of claim 13 wherein the at least one pneumatic cylinder is capable of maintaining a generally static traction force of greater than 111 N (25 pounds) for a period in excess of 10 minutes without additional pressurized air being injected into the at least one pneumatic cylinder.

16. The apparatus of claim 13 wherein the at least one pneumatic cylinder is capable of maintaining a generally static traction force of greater than 200 N (45 pounds) for a period in excess of 20 minutes without additional pressurized air being injected into the at least one pneumatic cylinder.

17. The apparatus of claim 13 comprising a gauge indicating traction force.

18. The apparatus of claim 13 comprising at least one pressure regulator adapted to prevent the pressure in the at least one pneumatic cylinder from exceeding a predetermined value.

19. The apparatus of claim 13 wherein the pressure relief mechanism is incorporated in the hand pump.

20. The apparatus of claim 13 wherein the at least one pneumatic cylinder comprises at least one pressure activated seal.

21. The apparatus of claim 13 wherein the at least one pneumatic cylinder comprises at least one pressure activated seal extending circumferentially around a piston.

22. The apparatus of claim 13 wherein the at least one pneumatic cylinder comprises at least one pressure activated seal extending circumferentially around a piston, the pressure activated seal movable between a relaxed position and an extended position so the pressure activated seal engages an internal surface on the pneumatic cylinder when the pneumatic cylinder is in the pressurized state.

23. The apparatus of claim 13 wherein the treatment period comprises at least 10 minutes.

24. A low-cost, light weight portable cervical traction device for home use by a patient comprising:
- a support structure having a track;
- a carriage slidable along a portion of the track, the carriage comprising a head support pad adapted to receive a patient's head and the restraining mechanism comprises a pair of opposing neck supports contoured and arranged to engage the occipital area of the patient's head when the head is on the head support pad, the restraining mechanism adapted to releasably restrain a portion of a patient's body to the carriage;
- pneumatic cylinder means for moving the carriage along the track relative to the support structure when in a pressurized state and for maintaining a generally static traction force during a treatment period when in the pressurized state without additional pressurized air being supplied;
- a hand pump operated by the patient fluidly connected to the pneumatic cylinder means and adapted to inject pressurized air into the pneumatic cylinder means; and
- a pressure relief mechanism operated by the patient adapted to release pressure from the pneumatic cylinder means.

25. A low-cost, light weight portable cervical traction device for home use by a patient comprising:
- a support structure having a track;
- at least one carriage slidable along a portion of the track, the carriage comprising a head support pad adapted to receive a patient's head and the restraining mechanism comprises a pair of opposing neck supports contoured and arranged to engage the occipital area of the patient's head when the head is on the head support pad, the restraining mechanism adapted to releasably restrain a portion of a patient's body to the carriage;

a pneumatic traction force generating apparatus comprising at least one pneumatic cylinder having a first end and a moveable piston at a second end, one of the pneumatic cylinder or the piston operatively coupled to a support structure, and the other operatively coupled to the carriage, the pneumatic traction force generating apparatus adapted to move the carriage along the track relative to the support structure when in a pressurized state and to maintain a generally static traction force during a treatment period when in the pressurized state without additional pressurized air being supplied;

a hand pump operated by the patient fluidly connected to the pneumatic traction force generating apparatus and adapted to inject pressurized air into the at least one pneumatic cylinder; and a pressure relief mechanism operated by the patient adapted to release pressure from the pneumatic traction force generating apparatus.

26. The apparatus of claim 25 wherein the restraining mechanism comprises a pair of opposing neck supports adjustably attached to the carriage to permit adjustment of the lateral separation there between.

27. The apparatus of claim 25 wherein the pneumatic traction force generating apparatus is capable of maintaining a generally static traction force of greater than 111 N (25 pounds) for a period in excess of 10 minutes without additional pressurized air being injected into the at least one pneumatic cylinder.

28. The apparatus of claim 25 wherein the pneumatic traction force generating apparatus is capable of maintaining a generally static traction force of greater than 200 N (45 pounds) for a period in excess of 20 minutes without additional pressurized air being injected into the at least one pneumatic cylinder.

29. The apparatus of claim 25 comprising a gauge indicating traction force.

30. The apparatus of claim 25 comprising at least one pressure regulator adapted to prevent the pressure in the pneumatic traction force generating apparatus from exceeding a predetermined value.

31. The apparatus of claim 25 wherein the pressure relief mechanism is incorporated in the hand pump.

32. The apparatus of claim 25 wherein the at least one pneumatic cylinder comprises at least one pressure activated seal.

33. The apparatus of claim 25 wherein the at least one pneumatic cylinder comprises at least one pressure activated seal extending circumferentially around the piston, the pressure activated seal movable between a relaxed position and an extended position so the pressure activated seal engages an internal surface on the pneumatic cylinder when the pneumatic cylinder is in the pressurized state.

34. The apparatus of claim 25 wherein the treatment period comprises at least 10 minutes.

35. A low-cost, light weight portable cervical traction device for home use by a patient comprising:

a support structure having a track;

a carriage slidable along a portion of the track, the carriage comprising a head support pad adapted to receive a patient's head and the restraining mechanism comprises a pair of opposing neck supports contoured and arranged to engage the occipital area of the patient's head when the head is on the head support pad, the restraining mechanism adapted to releasably restrain a portion of a patient's body to the carriage;

a pneumatic traction force generating means comprising at least one pneumatic cylinder means having a first end and a moveable piston means at a second end, one of the pneumatic cylinder means or the moveable piston means operatively coupled to a support structure, and the other operatively coupled to the carriage, the pneumatic traction force generating means for moving the carriage along the track relative to the support structure when in a pressurized state and for maintaining a generally static traction force during a treatment period when in the pressurized state without additional pressurized air being supplied;

a hand pump operated by the patient fluidly connected to the pneumatic traction force generating means and adapted to inject pressurized air into the at least one pneumatic cylinder means; and a pressure relief mechanism operated by the patient adapted to release pressure from the pneumatic traction force generating means.

36. A low-cost, light weight portable cervical traction device for home use by a patient comprising:

a support structure having a longitudinal axis;

a carriage slidable along a portion of the support structure parallel to the longitudinal axis, the carriage comprising a head support pad adapted to receive a patient's head;

a restraining mechanism comprising a pair of opposing neck supports contoured and arranged to engage the occipital area of the patient's head when the head is on the head support pad;

a pneumatic traction force generating apparatus comprising at least one air inlet, the pneumatic traction force generating apparatus operatively coupled to move the carriage relative to the support structure when in a pressurized state, the pneumatic traction force generating apparatus adapted to maintain a generally static traction force during a treatment period when in the pressurized state without additional pressurized air being supplied;

a hand pump operated by the patient adapted to inject pressurized air into the pneumatic traction force generating apparatus, the hand pump is capable of injecting at least 138 kPa (20 psi) of pressure into the pneumatic traction force generating apparatus; and a pressure relief mechanism operated by the patient adapted to release pressure from the pneumatic traction force generating apparatus.

37. The apparatus of claim 36 wherein pair of opposing neck supports comprise an adjustable attachment to the carriage that permits adjustment of the lateral separation there between.

38. The apparatus of claim 36 wherein the pneumatic traction force generating apparatus is capable of maintaining a generally static traction force of greater than 111 N (25 pounds) for a period in excess of 10 minutes without additional pressurized air being injected.

39. The apparatus of claim 36 wherein the pneumatic traction force generating apparatus is capable of maintaining a generally static traction force of greater than 200 N (45 pounds) for a period in excess of 20 minutes without additional pressurized air being injected.

40. The apparatus of claim 36 comprising a gauge indicating traction force.

41. The apparatus of claim 36 comprising at least one pressure regulator adapted to prevent the pressure in the pneumatic traction force generating apparatus from exceeding a predetermined value.

42. The apparatus of claim 36 wherein the pressure relief mechanism is incorporated in the hand pump.

43. The apparatus of claim 36 wherein the pneumatic traction force generating apparatus comprises at least one pneumatic cylinder.

44. The apparatus of claim 36 wherein the pneumatic traction force generating apparatus comprises at least one pneumatic cylinder including at least one pressure activated seal.

45. The apparatus of claim 36 wherein the pneumatic traction force generating apparatus comprises at least one pneumatic cylinder and at least one pressure activated seal in the pneumatic cylinder extending circumferentially around a piston, the pressure activated seal movable between a relaxed position and an extended position so the pressure activated seal engages an internal surface on the pneumatic cylinder when the pneumatic cylinder is in the pressurized state.

46. The apparatus of claim 36 wherein the treatment period comprises at least 10 minutes.

47. A low-cost, light weight portable cervical traction device for home use by a patient comprising:
   a support structure having a longitudinal axis;
   a carriage slidable along a portion of the support structure parallel to the longitudinal axis, the carriage comprising a head support pad adapted to receive a patient's head;
   a restraining mechanism comprising a pair of opposing neck supports contoured and arranged to engage the occipital area of the patient's head when the head is on the head support pad;
   pneumatic traction force generating means comprising at least one air inlet means, the pneumatic traction force generating means operatively coupled for moving the carriage relative to the support structure when in a pressurized state and for maintaining a generally static traction force during a treatment period when in the pressurized state without additional pressurized air being supplied;
   a hand pump operated by the patient adapted to inject pressurized air into the pneumatic traction force generating means, the hand pump is capable of injecting at least 138 kPa (20 psi) of pressure into the pneumatic traction force generating means; and
   a pressure relief mechanism operated by the patient adapted to release pressure from the pneumatic traction force generating means.

48. A low-cost, light weight portable cervical decompression device for home use by a patient comprising:
   a support structure having a longitudinal axis;
   a carriage slidable along a portion of the support structure parallel to the longitudinal axis, the carriage comprising a head support pad adapted to receive a patient's head;
   a restraining mechanism comprising a pair of opposing neck supports contoured and arranged to engage the occipital area of the patient's head when the head is on the head support pad;
   a pneumatic traction force generating apparatus comprising at least one air inlet, the pneumatic traction force generating apparatus operatively coupled to move the carriage relative to the support structure when in a pressurized state, the pneumatic traction force generating apparatus adapted to maintain a generally static force during a treatment period when in the pressurized state without additional pressurized air being supplied;
   a hand pump operated by the patient adapted to inject pressurized air into the pneumatic traction force generating apparatus, the hand pump is capable of injecting at least 138 kPa (20 psi) of pressure into the pneumatic traction force generating apparatus; and
   a pressure relief mechanism operated by the patient adapted to release pressure from the pneumatic traction force generating apparatus.

\* \* \* \* \*